United States Patent [19]

McCorkle, Jr.

[11] Patent Number: 4,582,056

[45] Date of Patent: * Apr. 15, 1986

[54] ENDOCARDIAL LEAD EXTRACTION APPARATUS AND METHOD

[76] Inventor: Charles E. McCorkle, Jr., 1427 E. Bayview Dr., Tempe, Ariz. 85283

[*] Notice: The portion of the term of this patent subsequent to Sep. 11, 2001 has been disclaimed.

[21] Appl. No.: 651,439

[22] Filed: Sep. 17, 1984

Related U.S. Application Data

[63] Continuation of Ser. No. 480,412, Mar. 30, 1983, Pat. No. 4,471,777.

[51] Int. Cl.⁴ ............................................. A61B 17/50
[52] U.S. Cl. ............................ 128/303 R; 128/419 P; 128/785; 294/100
[58] Field of Search ................ 128/127, 303 R, 304.5, 128/305.1, 310, 328, 334 R, 356, 419 P, 785; 294/92, 100, 115

[56] References Cited

U.S. PATENT DOCUMENTS

| | | | |
|---|---|---|---|
| 686,578 | 11/1901 | Bowersox | 128/356 |
| 1,083,103 | 12/1913 | Jentzsch | 128/343 |
| 2,212,013 | 8/1940 | Devareaux | 294/100 |
| 3,788,325 | 1/1974 | Jacobsen | 128/303 R |
| 3,964,468 | 6/1976 | Schulz | 128/321 |
| 4,038,987 | 8/1977 | Komiya | 128/321 |
| 4,046,149 | 9/1977 | Komiya | 294/100 |
| 4,198,960 | 4/1980 | Utsugi | 128/328 |
| 4,243,040 | 1/1981 | Beecher | 128/328 |
| 4,253,697 | 3/1981 | Acosta | 294/115 |

FOREIGN PATENT DOCUMENTS 2829159 1/1980 Fed. Rep. of Germany ...... 128/328
2945237 5/1981 Fed. Rep. of Germany ...... 128/328

Primary Examiner—William E. Kamm
Assistant Examiner—Mitchell J. Shein
Attorney, Agent, or Firm—Cahill, Sutton & Thomas

[57] ABSTRACT

A composite assembly includes a first catheter having a lead grasping mechanism extending through a channel thereof, a second catheter concentrically disposed over the first catheter and having a smooth, tapered end and a third catheter concentrically disposed over the second catheter and is used to remove an inoperative endocardial lead from a patient's heart through a venous path. A free end of the lead is grasped and held securely to the first catheter by a grasping mechanism. The second and third catheters then are slid as a unit through the venous path over the grasped end of the lead as opposing tensile force is maintained on the first catheter to prevent movement of the lead. The second catheter is rotated to cause its smooth, tapered, leading edge with outward sharp serrations to separate scar tissue from the lead and dilate a path through the scar tissue. The third catheter, which also has a smooth leading edge and outward sharp serrations is further advanced a predetermined amount forward over the second catheter and is rotated to separate and/or dislodge a tip of the lead which is embedded in scar tissue of the heart. The composite assembly along with the lead therein then is removed as a unit from the heart via the venous path without causing excessive forces to be applied to the vein or the wall of the heart.

7 Claims, 29 Drawing Figures

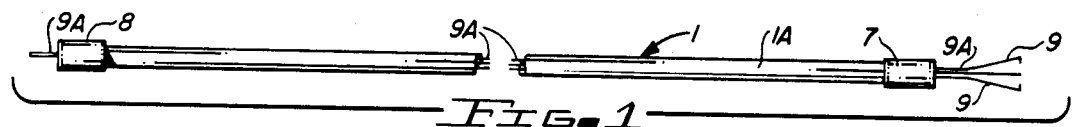
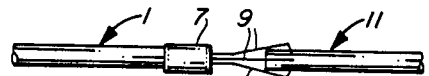
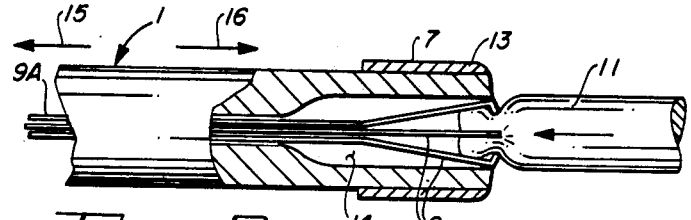
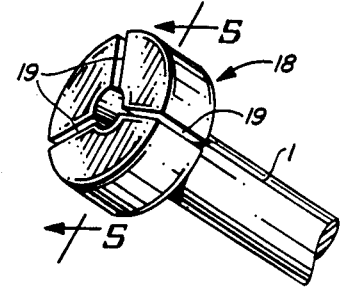
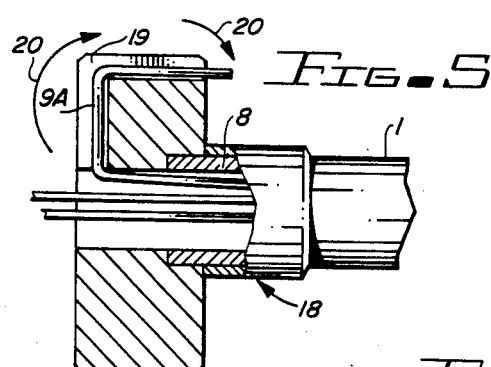
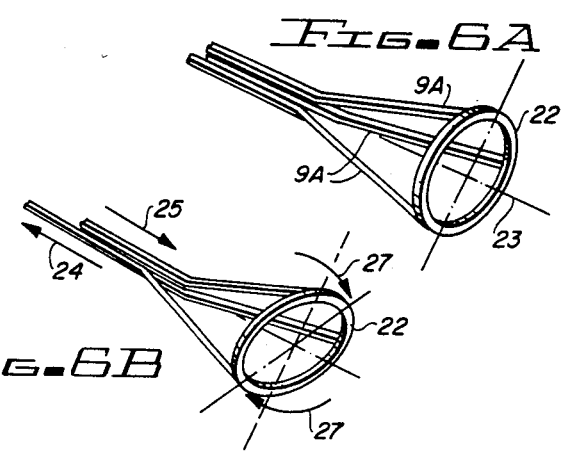
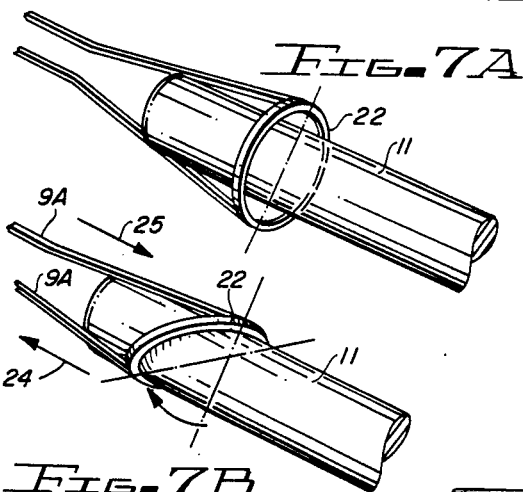
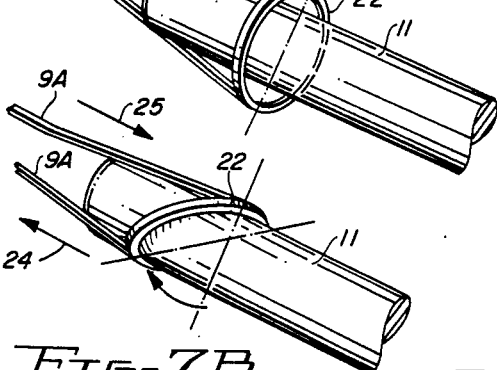
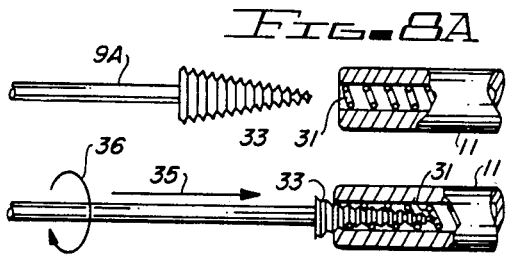
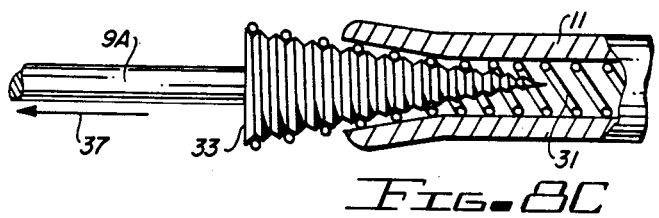

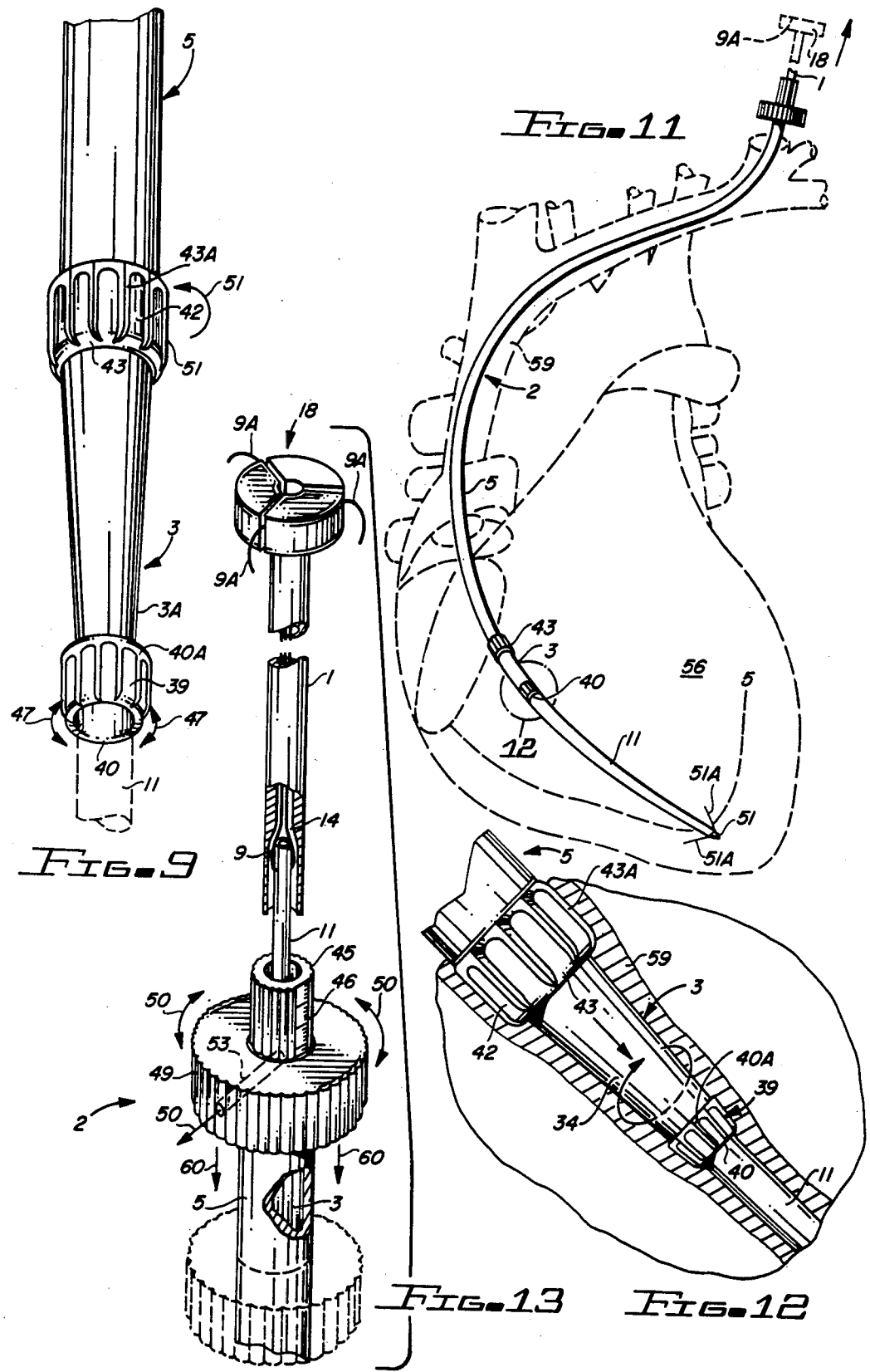

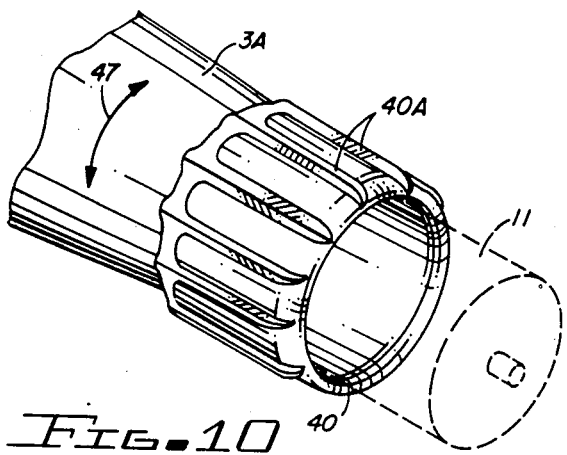
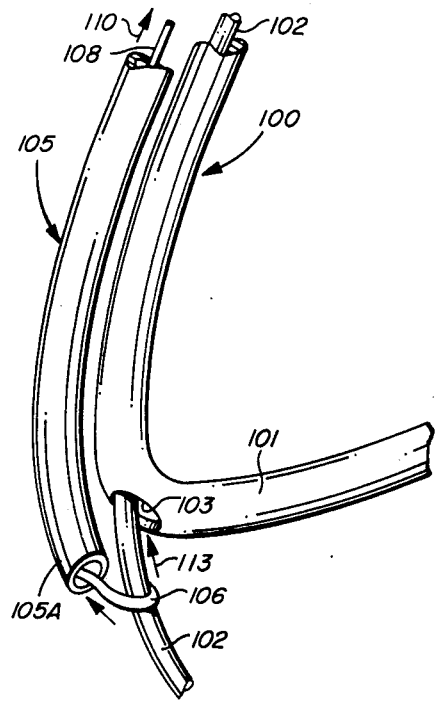
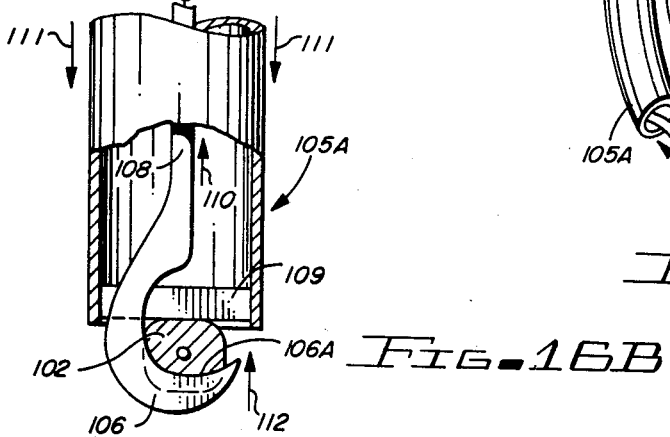
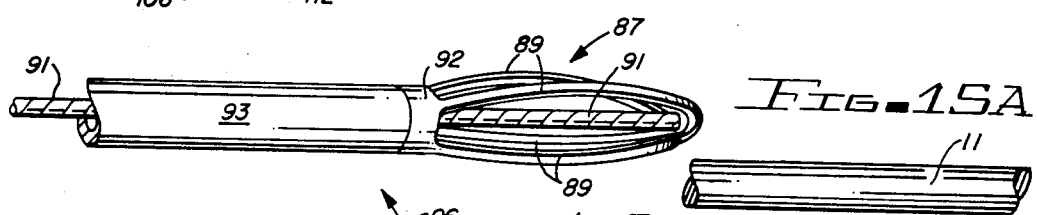
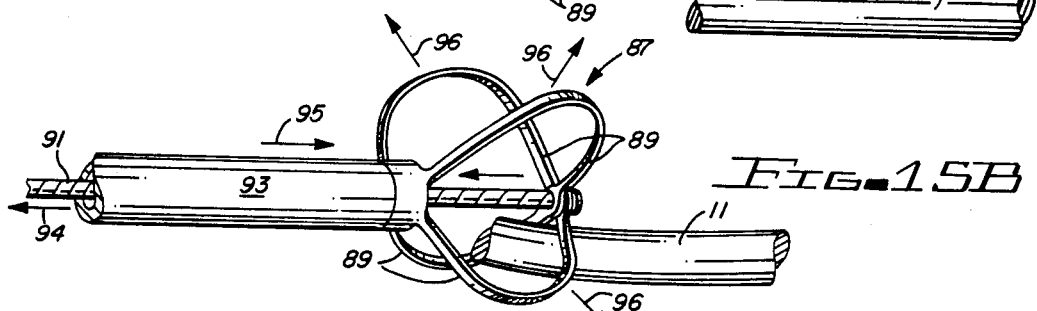
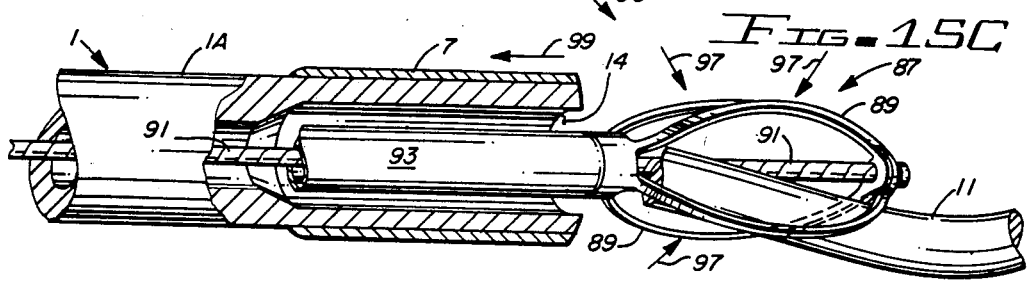

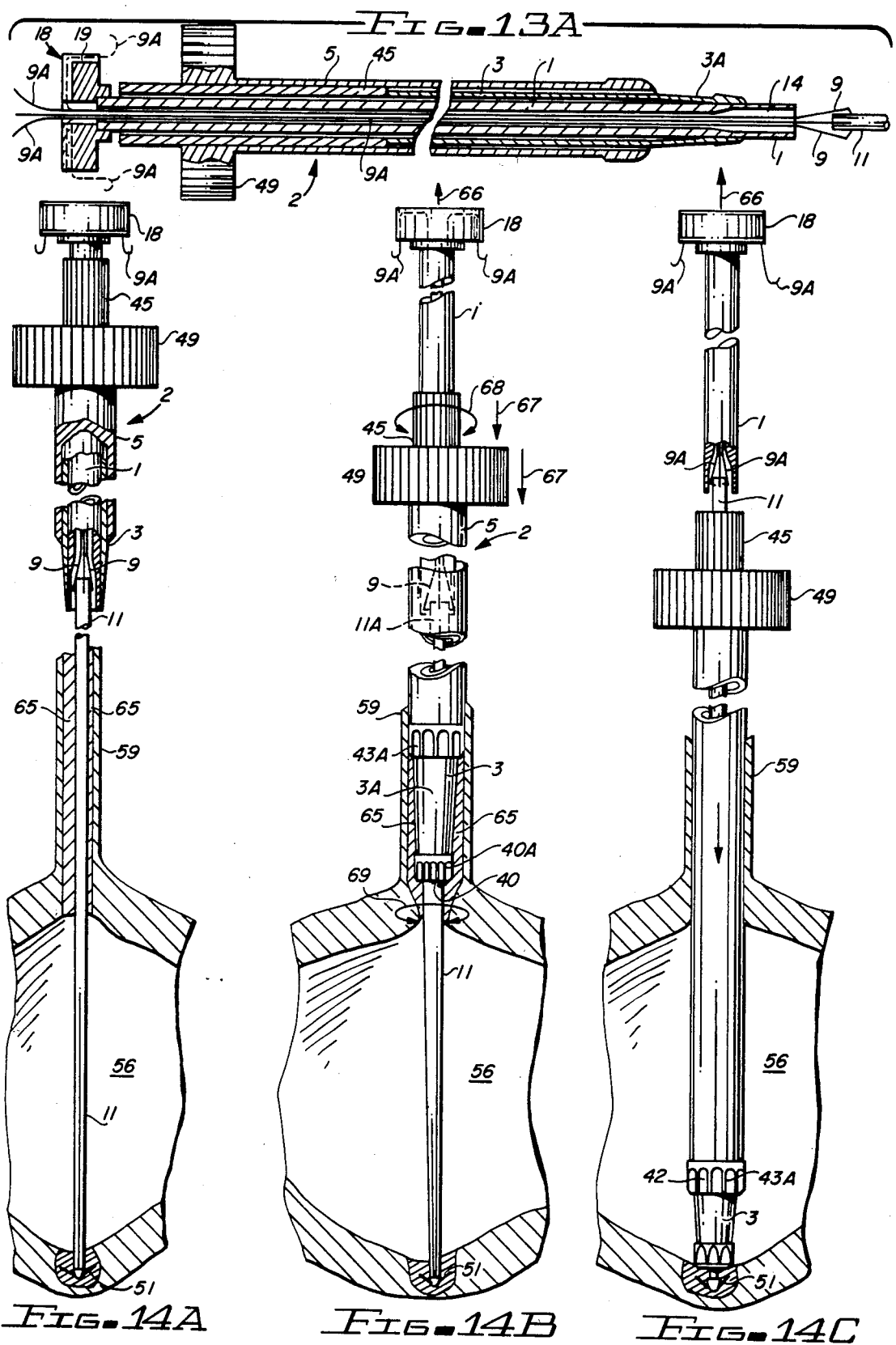

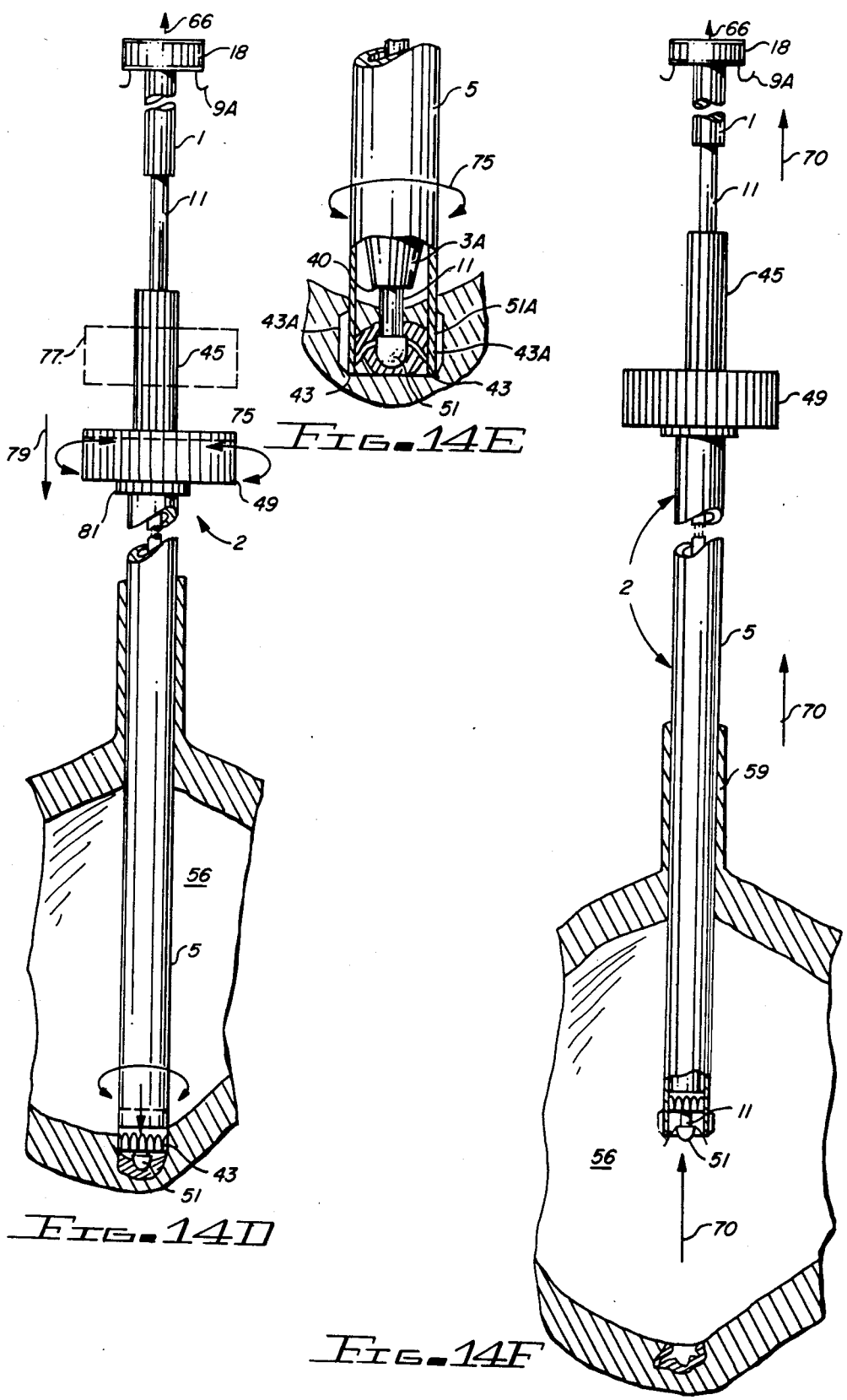

ENDOCARDIAL LEAD EXTRACTION APPARATUS AND METHOD

This is a continuation, of application, Ser. No. 480,412, filed 3/30/83 now U.S. Pat. No. 4,471,777.

BACKGROUND OF THE INVENTION

The invention relates to methods and apparatus for removal of transvenous endocardial leads from a patient's heart and the venous path thereto.

In the past, various types of endocardial leads and electrodes thereof have been introduced into different chambers of a patient's heart including the right ventrical, right atrial appendage, and atrium as well as the coronary sinus. These flexible leads usually are composed of an insulator sleeve that contains an implanted helical coil conductor that is attached to an electrode tip. This electrode is placed in contact with myocardial tissue by passage through a venous access, often the subclaven vein or one of its tributories, which leads to the endocardial surface of the heart chambers. The tip with the electrode contact is held in place by trabeculations of myocardial tissue. The tips of many available leads include flexible tines, wedges, or finger-like projections which extend radially outward and usually are molded from and/are integral with the insulating sheath of the lead. These tines or protrusions allow surrounding growth of tissue and scar in chronically implanted leads to fix the electrode tip in position in the heart and prevent dislodgement of the tip during the life of the lead. In "acute placement+ of the electrode or tip a blood clot forms about the flanges or tines (due to enzymes released as a result of irritation of the trabeculations of myocardial tissue by the presence of the electrode tip) until scar tissue eventually forms, usually in three to six months. The tines or wedges or finger-like projections allow better containment by the myocardial trabeculations of muscle tissue and prevent early dislodgement of the lead tip. Other types of "screw-in" tips include the electrodes described in U.S. Pat. Nos. 4,209,019 and 3,974,834, assigned to Medtronic, Inc. Although the state of the art in implemented pulse generator or pacemaker technology and endocardial lead technology has advanced considerably, endocardial leads nevertheless occasionally fail, due to a variety of reasons, including breakage of a lead, insulation breaks, breakage of the inner helical coil conductor thereof and increase in electrode resistance. Also, in some instances, it may be desirable to electronically stimulate different portions of the heart than are presently being stimulated with leads already in place. There are a considerable number of patients who have one or more, and sometimes as many as four or five unused leads in their veins and heart.

Although it obviously would be desirable to be able to easily remove such unused leads, in the past surgeons usually have avoided attempts to remove inoperative leads because the risk of removing them exceeded the risk of leaving them in. The risks of leaving unused myocardial leads in the heart and venous path include increased likelihood that an old lead may be the site of infection which may necessitate removal of the lead to prevent continued bacteremia and abcess formation which, in turn, may lead to fatal complications. Furthermore, there is an increased likelihood of the formation of blood clots in the atrial chamber about entangled leads. Such clots may embolize to the lung and produce severe complications and even fatality. Furthermore, the presence of unused leads in the venous pathway and inside the heart can cause considerable difficulty in the positioning and attachment of new endocardial leads in the heart.

Thus, it is clear that the potential for infection and other complications increases rapidly as a number of old or unused endocardial leads in the heart and venous pathway increases.

Removal of an inoperative lead sometimes can be accomplished by applying traction and rotation to the outer free end of the lead but only if done prior to fixation of the lead tip in the trabeculations of myocardial tissue by scar formation or large clot development. Even then, it is possible that a clot has formed so the removal of the leads causes various sized emboli to pass to the lungs, producing severe complications.

In cases where the lead tip has become attached by scar tissue to the myocardial wall, removal of the lead always has presented major problems and risks. Porous lead tips that are sometimes used may have ingrowth of scar tissue attaching them to the myocardial wall. Sufficient traction on such leads in a removal attempt could cause disruption of the myocardial wall prior to release of the embedded lead tip, causing fatality. The tines or flanges of other types of leads that are not tightly scarred to the myocardial wall present similar risks. Even if screw-in tip electrodes of the kind mentioned in the Medtronic patents referred to above are used, wherein the tips theoretically can be unscrewed from the myocardial wall, unscrewing of such tips may be prevented by a channel of scar tissue and endothelium that surrounds the outer surface of the lead along the venous pathway. Such "channel scar" tissue prevents withdrawal because of tight encasement of the lead. Continual strong pulling or twisting of the outer free end of the lead could cause rupturing of the right atrial wall or right ventricular wall if there is such tight circumferential encasement of adherent channel scar tissue in the venous path. Such tight encasement by scar tissue in the venous pathway and in the trabeculations of the myocardial wall typically occurs within six months to a year of the initial placement of the lead.

The risks of removal of a lead by such traction and rotation of the lead are so high that if it becomes imperative that the lead be removed (as in the case of infection) most surgeons have elected to open the patient's chest and surgically remove the lead rather than attempt removal by applying traction and rotation thereto.

Clearly, there is a need for an improved method and apparatus for extracting "chronically placed" endocardial leads with minimal risk to the patient.

Accordingly, it is an object of the invention to provide an improved method and apparatus for extraction of endocardial leads with minimal risk to the patient.

It is another object of the invention to allow placement of new endocardial leads and electrodes without interference by old leads in the venous path or heart with the new leads.

It is another object of the invention to provide a method and apparatus for removal of infected leads without the need for open chest surgery.

SUMMARY OF THE INVENTION

Briefly described, and in accordance with one embodiment thereof, the invention provides a method and apparatus for removing an inoperative endocardial lead from a patient's heart through a venous pathway by controlling a "lead grasping" mechanism which may extend through a first catheter to securely attach a free end of the lead to the leading end of the first catheter and, while maintaining tension on the lead grasping mechanism, sliding a second catheter disposed concentrically about the surface of the first catheter over the attached end of the lead and along the insulating surface of the lead to separate any adherent scar tissue from the surface of the lead and, if necessary, dilating the venous path as the second catheter is advanced toward the tip of the lead, which tip is tightly embedded in the wall of the heart by scar tissue. In the described embodiments of the invention, the leading edge of the second catheter is tapered, is very smooth, and is outwardly serrated to enhance separation of the adherent scar tissue in the venous channel from the surface of the lead and also to enhance dilation of the venous path if necessary.

The tip portion of the second catheter is radiopaque to allow fluorescent visualization of the position of the radiopaque tip as the second catheter is advanced to the embedded tip of the lead. A third catheter is concentrically disposed about the second catheter and initially has a radiopaque, smooth outwardly serrated leading edge positioned adjacent to the beginning of the tapered end portion of the second catheter. Both the second catheter and the third catheter are composed of semi-rigid but somewhat flexible plastic material. Both are advanced as a unit as tension is maintained on the first catheter and the lead attached thereto so they remain relatively stationary. As the leading end of the second catheter is advanced through the venous pathway, the second and third catheters are rotated together, causing the outward serrations of the second catheter tip to enhance the separation of adherent scar tissue from the lead. The smooth outwardly serrated edge of the third catheter further clears the pathway through the venous channel, if necessary. After the leading portion of the second catheter has reached a shoulder of the embedded lead tip, the third catheter is slid forward over the second catheter and is rotated relative to the second catheter so that its outward serrations separate scar tissue surrounding the embedded lead tip and/or forces the scar tissue to break loose from the lead tip. At this point, the endocardial lead has its forward portion entirely inside the second catheter. The endocardial lead, the second catheter, and the third catheter are removed as a unit from the heart through the venous pathway and out of the patient.

In the described embodiments of the invention, the first, second and third catheters are preassembled. Several embodiments of the grasping mechanism are described, including a first embodiment with three or more outwardly sprung grasping fingers each with an inwardly oriented claw and each attached to a stylet that extends through the channel of the first catheter and through a locking head disposed at the outer a distal end of the first catheter. The first catheter has a reinforced, slightly enlarged chamber at its leading end. The open grasping fingers or claws are positioned around the free end of the endocardial lead. While traction is applied on the stylet wires at the opposite end of the first catheter to maintain the position of the lead, the first catheter is slid forward, its reinforced end portion forcing the claws or fingers together, causing them to close on and grasp the free end of the lead and hold it within the enlarged chamber. The locking head has slots for receiving the end portions of the stylet wires and holding them in place, thereby maintaining tension thereon and holding the lead securely in the enclosed chamber. In another embodiment of the grasping mechanism, a circular or oval loop has attached thereto two or more stylet wires that extend through the center of the first catheter and are manipulated at the opposite or outer end of the first catheter to tilt the loop after it has been positioned around the free end of the lead, thereby engaging the free end thereof. The leading end of the first catheter is slid so that its enlarged chamber slides over the tilted loop and the free end of the grasped lead. The stylet wires are bent into the slots of the locking head, thereby maintaining tension on the grasping mechanism. In a third embodiment of the grasping mechanism, a screw-type end is provided on the end of cable element extending through the first catheter and is rotated to screw it into the helical coil portion of the free lead end.

In a fourth embodiment of the grasping mechanism, a device known in the art as a "basket" is used. The basket grasper includes a number of arc-shaped spring elements all connected at the rear end thereof to an eyelet or small loop through which a control stylet passes. The front end of the control stylet is attached to the forward ends of all of the arc-shaped spring elements. Normally, with no tension on the stylet, the basket is held in an elongated shape by the natural spring bias of the arch-shaped spring elements. When sufficient tension is maintained on the controlled styled pulling it rearward and the position of the stylet or loop is maintained, these forces cause the arc-shaped spring elements to bow outward, increasing the widths of the gaps between the various mutually adjacent arc-shaped spring elements. The position of the eyelet or loop is maintained by means of a flexible, semi-rigid tube or catheter through which the control stylet extends. The tube and the control stylet can extend through the center of the first catheter. The collapsible basket can be positioned so that the free end of the endocardial lead or some other portion thereof extends into one of the above-mentioned gaps. The tension on the controlled stylet then is released, causing two-adjacent arc-shaped spring elements to close tightly upon the portion of the lead extending into the gap between those two arc-shaped spring elements. The basket and the portion of the lead grasped thereby then are pulled into the enlarged chamber at the proximal end of the first or lead grasping catheter.

The described second and third catheters have reinforced leading tip portions into which plastic or metal inserts having smooth leading edges with sharp outward serrations are inserted. At the trailing end of the second catheter, an elongated torquing handle concentrically disposed about the first catheter is attached to allow rotation of the second catheter relative to the first catheter, thereby allowing rotation of the serrated tip of the second catheter as it is advanced through the scar tissue in the venous channel. This enchances separating of the scar tissue by the serrated edge. An enlarged second torquing handle is attached to the trailing end of the third catheter and disposed concentrically about the first torquing handle. Initially, the second torquing handle is locked to the first torquing handle so that the second and third catheters rotate together. The locking means is disengaged after the leading end of the second catheter has been advanced to its final position, allowing the second torquing handle to be rotated relative to the first, thereby rotating the serrated tip of the third catheter and allowing it to separate scar tissue from the embedded tip as the third catheter is advanced a measured amount. The distance through which the third catheter is advanced over the second catheter is gauged by means of a scale on the first torquing handle as the second torquing handle is slid along it.

In one described embodiment of the invention, the lead to be removed has broken inside the heart or the venous path, so its free outer end is not accessible near the pulse generator. In this instance, a COOK introducer is used to position an open channel shaft through an opening into the vein and through the vein to a location adjacent to the free end of the broken lead. The multi-catheter lead extracting assembly of the invention is guided, by means of fluoroscopic visualizing of a radiopaque tip of the first (lead-grasping) catheter, through the open channel of the shaft so that the open grasping mechanism surrounds the free end of the lead. The stylet wires through the first catheter are manipulated to close the grasping mechanism and attach it securely to the leading end of the first catheter. The method of extracting the lead from this point on is as previously described.

If a composite dual lead of the type described in my U.S. Pat. No. 4,332,259 is in place in a patient and must be exracted, the method and apparatus of the present invention can be used as explained previously, but first one of the leads, for example, the core lead, must be severed from the other. In order to accomplish this, a COOK introducer is used as described above to position an open channel shaft or tube through an opening into the vein so that the proximal end of the open shaft or tube is adjacent to the point at which it is desired to sever the cord lead extending out of the channel lead, typically into the ventrical of the patient's heart. A semi-rigid catheter with a stop bar in its proximal end and a J-shaped or sickle-shaped inner knife edge attached to the proximal end of a control stylet extending through the catheter are inserted through the open channel shaft. The sickel-shaped knife element is extended beyond the proximal end of the subject catheter and is guided under fluoroscopic visualization to loop around the core lead and pull it against the stop bar in the end of the catheter. Sufficient tension is applied to the control stylet to cause the knife edge to cut through the core lead. The upper portion of the core lead is withdrawn into the channel lead. The catheter and knife therein are withdrawn from the vein. The separated channel lead and core lead portions of the composite dual lead assembly then can be removed one at a time using the previously described extracting apparatus and method.

BRIEF DESCRIPTION OF THE DRAWINGS

FIG. 1 is a partial elevation view of the first or lead grasping catheter of the present invention.

FIG. 2 is a partial elevation view illustrating the grasping mechanism of the device shown in FIG. 1.

FIG. 3 is a partial cutaway view illustrating the leading end of the lead grasping catheter of FIG. 1 grasping an endocardial lead.

FIG. 4 is a partial perspective view of a locking head which is attached to the trailing end of the lead grasping catheter of FIG. 1.

FIG. 5 is a partial section view useful in illustrating and explaining the locking head shown in FIG. 4 and is a section view along section line 5—5 of FIG. 4.

FIGS. 6A and 6B are partial diagrammatic perspective views useful in illustrating another embodiment of a lead grasping mechanism used in conjunction with a lead grasping catheter similar to the one shown in FIG. 1.

FIGS. 7A and 7B are partial perspective diagrammatic views useful in illustrating the use of the lead grasping mechanism shown in FIGS. 6A and 6B.

FIGS. 8A, 8B and 8C are partial cutaway elevation views useful in illustrating a third lead grasping mechanism that can be used in conjunction with the lead grasping catheter of FIG. 1.

FIG. 9 is a partial elevation view showing the dilating catheter and outer ensheating catheter of the endocardial lead extraction apparatus of the present invention.

FIG. 10 is a partial perspective view illustrating the serrated leading edges of either the dialating catheter or the outer ensheating catheter of the present invention.

FIG. 11 is a diagram of a heart in which an endocardial lead to be removed is illustrated, the lead extraction apparatus of the present invention being shown in a partly advanced location along the lead.

FIG. 12 is an enlarged view of detail 12 of FIG. 11.

FIG. 13 is a partial cutaway perspective view useful in explaining use of the endocardial lead extraction system of the present invention.

FIG. 13A is a partial section view useful in describing the endocardial lead extraction system of the present invention.

FIGS. 14A-14F include a sequence of a partial cutaway elevation views useful in describing utilization of the endocardial lead extraction apparatus of the present invention to extract an endocardial lead embedded in a patient's heart.

FIGS. 15A-15C are partial perspective views of an alternate lead grasping mechanism.

FIGS. 16A and 16B are diagrams useful in explaining how to pre-cut a composite dual lead assembly prior to using the lead extracting apparatus of the invention.

DESCRIPTION OF THE INVENTION

Referring now to the drawings, the endocardial lead extraction assembly of the present invention will now be described. Although the device is assembled prior to use and has the configuration indicated in FIGS. 9, 11, 13, 13A and FIGS. 14A-F, it will be helpful to understanding of the invention to individually describe and illustrate three catheters of which the assembly is composed. The inner catheter will be referred to by reference numeral 1 and is referred to herein as the "lead grasping catheter". Several embodiments of the lead grasping mechanism thereof are described in FIGS. 1 through 8C. The second catheter that is concentrically disposed about the lead grasping catheter 1 is referred to hereinafter as the "dilating catheter" and is designated by reference numeral 3. The third catheter, which is concentrically disposed about the dilating catheter 3, is referred to hereinafter as the "ensheathing cather" and is designated by reference numeral 5.

Referring now to FIG. 1, one embodiment of lead grasping catheter 1 includes a flexible tube or sheath 1A having a leading end 7 and a trailing end 8. The leading end 7 is the end which is first inserted into the venous pathway through which the inoperative lead is to be removed. Protruding from leading end 7 of grasping catheter 1 are three or more grasping claws designed by reference numeral 9. Grasping claws 9 are sprung outward, as shown, and each is connected to a separate stylet, generally designated by reference numeral 9A. The stylets 9A extend through the entire length of the channel of grasping catheter 1 and extend an appreciable distance beyond the trailing or proximal end 8 of grasping catheter 1.

Referring now to FIG. 2, reference numeral 11 designates an end portion of an inoperative lead 11 which is to be removed. Usually the free end of lead 11 is obtained when the lead is cut loose from an implanted pulse generator in the patient, or else it is a free end of a portion of the lead that is broken either in the venous pathway to the heart or in the heart chamber itself. In any case, the open claws 9 are positioned around the free end of lead 11. Referring now to FIG. 3, it should be noted that leading end 7 of lead 1 is reinforced, for example, by means of a collar 13. The channel through lead grasping catheter 1 has a reinforced, enlarged opening or chamber 14 in its lead end. The chamber 14 is large enough that when a tension or traction force is applied on stylets 9A at the distal end of grasping catheter 1 in a direction indicated by arrow 15, and then the grasping catheter 1 is advanced along the stylets 9A, which are being held stationary, toward lead 11 in the direction indicated by arrow 16, the lead end 7 and the outer lip of chamber 14 will slide along the outwardly sprung claws 9, forcing them to close upon and grasp the extreme end portion of lead 11, as illustrated in FIG. 3. In accordance with the invention, the tensile force on stylus 9A holds them stationary as the grasping catheter 1 moves forward until the grasped free end of lead 11 is securely positioned in and held inside chamber 14. The, for all practical purposes of the invention, the free end of lead 11 is unitary with grasping catheter 1.

Although not shown in FIG. 1, trailing end edge 8 of grasping catheter 1 has preassembled thereon a locking head 18, shown in FIG. 5 in a partial sectional view and also shown in FIG. 4. Locking head 18 has as many slots 19 therein as there are stylet wires 9A and claws 9, typically three or four. After the lead 11 has been grasped and drawn into enlarged chamber 14 (FIG. 3), the three shown stylet wires 9A are bent outwardly and around into the three slots 19, in the directions indicated by arrows 20 in FIG. 5. This retains claws 9 and the grasped end of lead 11 securely in chamber 14, maintaining grasping catheter 1 and lead 11 as a unitary member or "cord" during the remainder of the lead extraction operation.

FIGS. 6A, 6B, 7A and 7B disclose an alternate lead grasping apparatus to claws 9. Referring now to FIG. 6A, a round stainless steel loop 22 is shown having three equally spaced peripheral points attached to three stylets 9A-1, 9A-2, and 9A-3. Initially, the plane of loop 22 is approximately perpendicular to the axis 23 of the stainless steel stylets 9A, extending through the channel of lead grasper tube 1A. As indicated in FIG. 6B, by applying opposed forces 24 and 25 to different ones of the stylets, the plane of loop 22 can be tilted in the directions indicated by arrows 27. Referring now to FIG. 7A, it can be seen that when loop 22 is perpendicular to the axis of the lead grasper channel, the loop 22 is positioned around the free end of myocardial lead 11. (Note that for convenience of illustration in FIGS. 6A, 6B, 7A and 7B the grasping catheter tube 1A is omitted).

As shown in FIGS. 7A, loop 22 is positioned around the free end of endocardial lead 11, and then opposed forces 24 and 25 are applied to the sylet wires as shown in FIG. 7B in order to tilt the loop 22. The tilted loop 22 thereby grasps the free end of lead 11. The leading end 7 is moved forward in the direction indicated by arrow 16 in FIG. 3 as described above, until loop 22 and the free end of lead 11 are tightly encompassed in chamber 14, accomplishing, in essence, the same result as claws 9.

As previously mentioned, endocardial leads ordinarily have a helical coil therein. Reference numeral 31 in FIGS. 8A-8C designates such a helical coil. In accordance with another embodiment of the invention, a single stylet 9A has a screw-tip 33 on the end thereof. As before, the grasping catheter tube 1A is omitted for simplicity of illustration. Referring to FIG. 8B, the screw-tip 33 is screwed into the helical coil 31 as the grasping catheter is moved forward in the direction of arrow 35 and rotated in the direction of arrow 36.

Referring to FIG. 8C, which shows the details somewhat enlarged, force 37 is applied to stylet 9A after screw tip 33 has securely engaged the free end of lead 11 to draw it into the chamber 14 (FIG. 3) of grasping catheter 1.

Usually, the claws 9 and stylets 9A or the loop 22 or the screw tip 33 would be made of flexible stainless steel. It is anticipated that other forms of grasping elements or control elements therefor will be designed as the technology develops.

The lead grasping catheter tube 1A is of slightly larger outside diameter than the insulating sheath of the lead 11. As will become apparent, the length of the grasping stylets 9A and the catheter tube 1A must be longer than the subsequently described dilating catheter 3, which has a still shorter ensheathing catheter 5 thereon.

FIGS. 15A-15C illustrate the use of another lead grasping device which is referred to by reference numeral 87, and is referred to as a "basket". Devices of this general type are commercially available and are used for capturing gall stones. Basket 87 includes a plurality of stainless steel, flat spring elements 89 which at their proximal end are connected together to a stylet 91. Arc-shaped spring members 89 are also connected together at their rear end by means of a collar, to which is attached the proximal end of a semi-rigid catheter 93. Control stylet 91 extends through the center of catheter 93. Basket 87, as shown in FIG. 18A is shown in its normal position (with no tension being applied to control stylet 81) adjacent to a free end of endocardial lead 11 which is to be extracted. In use, the stylet 91 and catheter 93 extend through the center of lead grasping catheter tube 1A, as indicated in dotted lines in FIG. 15C. Basket 87 extends beyond the enlarged chamber 14 at the reinforced end 7 of grasping catheter 1. To actuate basket 87 as a grasping mechanism, the user applies a tensile force 94 to the distal end of control stylet 91, while maintaining an opposing force 95 on the distal end of semi-rigid catheter 93, thereby causing the arc-shaped spring elements 89 to bow outward in the directions of arrows 96, as shown in FIG. 15B. This allows the free end (or some other portion) of lead 11 to fit between any of the gaps between adjacent arc-shaped springs 89, as shown in FIG. 15B. Once this configuration has been achieved, the next step in the method of use of basket 89 is to release the tension on control stylet 91, causing the arc-shaped spring elements 89 to collapse in the direction of arrows 97, as shown in FIG. 15C, whereby the two arc-shaped springs 89 tightly close upon and tightly grasp a portion of endocardial lead 11. Finally, by applying a force in the direction of arrow 99 to both the semirigid catheter 93 and control stylet 91, the entire basket 87 with lead 11 grasped thereby can be pulled into the reinforced enlarged chamber 14 at the proximal end of grasping catheter 1. This causes the arc-shaped springs 89 to close even more tightly on lead 11. If by chance the free end of lead 11 extends out of the gap between two adjacent arc-shaped springs 89 the leading edge of reinforced tip 7 of grasping catheter 1 will engage that portion of the lead 11, forcing it to the forward-most portion of the gap between the two arc-shaped leads 89 between which lead 11 is lodged, as basket 87 is drawn into enlarged chamber 14, even further improving the secureness with which basket 87 grasps lead 11.

Next, the dilating catheter 3 and its ensheathing catheter 5 will be described with reference to FIGS. 9-13A.

The leading or proximal end of dilating catheter 3 includes a radiopaque tip portion 39 by means of which the position of dilating cather 3 can be fluoroscopically visualized as the lead extracting assembly 2 (FIG. 14A) is advanced through the venous pathway. The extreme leading end of dilating catheter 3 has a smooth edge designated by reference numeral 40. As seen best in FIG. 10, sharp outward serrations or ridges 40A for separating venous scar tissue from lead 11 are disposed over the tip of dilating catheter 3 behind smooth leading tip 40. This tip can be composed of plastic, or metal, such as stainless steel in the form of an insert which slides into the end portion of dilating cather 3. It is essential that the leading edge 40 of dilating catheter 3 be very smooth in order to avoid cutting into the relatively soft outer sheath of lead grasping catheter 1, especially when catheter 1 is bent, as dilating catheter 3 slides forward over lead grasping catheter 1. It is also necessary that the sharp serrations or ridges or teeth 40A be provided behind the smooth leading edge 40 so that as dilating catheter is rotated in opposite directions indicated by arrows 47 as it is advanced, the serrations or ridges 40A will separate scar tissue in the venous pathway from the surface of lead 11.

The leading tip of outer ensheathing catheter 5 also has a smooth leading edge with sharp outward serrations designed by reference numeral 43. Immediately following smooth leading edge 43 are a plurality of spaced sharp serrations or ridges 43A similar to serrations 40A. The sharp outward oriented serrations 40A and 43A extend from just behind the smooth leading edges of the respective catheters to a distance behind the leading edges in order to ensure effective separation of the most dense and/or adherent channel scar tissue likely to be encountered. Ensheathing catheter 5 has an inside diameter that closely matches the outside diameter of dilating catheter 3A up to the beginning of a tapered end portion 3A. FIG. 9 shows an enlarged view of the leading end of dilating catheter 3 and ensheathing catheter 5. In FIG. 9, endocardial lead 11 is assumed to be attached in the manner previously described to the leading end of lead grasping catheter 1. It is assumed that dilating catheter has been slid over the grasped end of lead 11 and has further been slid a distance along its surface.

The inner channel surfaces of catheters 3 and 5 are very smooth to allow smooth sliding thereof. If needed, suitable lubricants, such as hydrophillic compounds, are used to coat the surfaces.

The configuration of the trailing end of the lead extracting assembly 2 is shown in FIG. 13 after lead 11 has been drawn entirely through the channel of dilating catheter 3.

The distal end of dilating catheter 3 is attached to a first torquing knob or handle 45, the outer edge of which is roughened to enable the user to easily grasp it between his thumb and forefinger. A measurement scale 46 is printed on the surface of inner knob 45.

The user can, by grasping inner knob 45 between his thumb and fingers, rotate inner knob 45 and thereby also rotate dilating catheter 3 in the directions indicated by arrows 47 in FIGS. 9 and 10. As subsequently explained, the sharp, outward serrations 40A thereby separate scar tissue that is adherent to lead 11. The tapered end portion 3A of dilating catheter 3 then effectively dilates a venous pathway through the scar tissue therein. This allows free passage of the lead extracting assembly 2 into and out of the heart.

Referring again to FIG. 13, an outer knob or handle 49 is attached to ensheathing catheter 5, so that when outer knob 49 rotates in the direction of arrows 50 (FIG. 13), ensheathing catheter 5 correspondingly rotates in the directions indicated by arrow 51 in FIG. 9.

A removable locking pin 53 extends through a hole in outer knob 49 into a corresponding hole in inner knob 45 to thereby lock inner knob 45 and outer knob 49 during the initial part of the lead removal process. Later, pin 53 is removed in the direction indicated by arrow 54 (FIG. 13) to allow outer knob, 49 and ensheathing catheter 5 to be rotated independently of inner knob 45 and dilating catheter 3.

To better understand the environment in which endocardial lead 11 exists and from which it must be removed, FIG. 11 shows a diagrammatic view of a heart in dotted lines. Reference numeral 56 generally designates the right ventrical. Reference numeral 51 designates a lead tip that is embedded by scar tissue to the myocardial trabeculations. Reference numeral 59 designates the vein through which the lead 11 is to be removed. In FIG. 11, the lead extracting assembly 2 is already partially inserted into the right ventrical. Detail 12 is shown in enlarged form in FIG. 12, giving a good view of the leading tapered end 3A of dilating catheter 3 and the leading portion of the ensheathing catheter 5 prior to removal of locking pin 54 (FIG. 13) to allow lateral and rotary movement of outer 49 relative to inner knob 45 in the directions indicated by arrows 60 and 50, respectively.

In FIG. 11, reference numeral 51A designates flexible tines of the type previously described, which are molded from the flexible material of which the outer sheath of endocardial lead 11 is made in order to facilitate formation of scar tissue embedding the tip 51 of lead 11 into the trabeculations of the myocardial tissue.

FIG, 13A is a partial sectional view of the lead extracting assembly 2 with the grasping claws 9 positioned about the free end of lead 11, but before they have been drawn into enlarged chamber 14 of lead grasping catheter 1.

It should be noted that the inner channel of dilating catheter has very low friction, which can be created by providing very smooth mating surfaces on the semirigid but flexible material from which the dilating catheter is formed or, as previously mentioned, by a special inner coating of hydrophyllic material. The friction needs to be low enough that it allows the channel dilator 3 to pass over the surface of grasping catheter 1 and also the outer surface of the endocardial lead 11 which is to be removed from the patient's heart. The same is true of the inner surface of ensheathing cather 5. The dilating catheter 3 and ensheathing catheter 5 can, for example, be composed of the same general type of low friction coefficient material of which the well known subsequently described COOK introducers are commonly made. The outward serrations can be molded from the same material, if desired, instead of using stainless steel inserts. In the configuration of the lead extracting assembly 2 at the beginning of the lead extraction procedure, the outwardly serrated end of the ensheathing catheter is positioned at the point where the tapered portion 3A of the dilating cather 3 begins, as shown in FIG. 14B.

To explain one example of the method of the present invention, the lead extraction assembly 2 is used in a typical situation in which the upper or distal end of the lead 11 to be removed is disconnected from the pulse generator or pacemaker device. The free end of that lead is freed of tissue down to the venous access port (unless the lead has been broken inside the venous pathway or in a chamber of the heart; the procedure for removal in this case is described subsequently). All of the usual ties around the lead sheath are removed.

The patient has been placed on a fluoroscopy table for visualization (by means of X-rays) of the position of the faulty lead in the venous channel on the heart. The helical coil through the center of the lead to be removed makes X-ray visualization of its position possible. Usually, the skin in the pectoral area where the pulse generator is implanted is opened. The pulse generator is removed. The connector assembly that connects the lead to the pulse generator is cut off. The cut free end of the lead can be grasped by any of the above-mentioned embodiments of the lead grasping mechanism. If the grasping claws 9, shown in FIGS. 1-3, are utilized, the lead end protruding from the access hole in the vein is grasped as shown in FIG. 3 and pulled into the enlarged chamber 14 of the lead grasping catheter 1. The stylets 9A then all are bent around and into the respective grooves 19 of the stylet locking head 18 (in the manner previously explained) to retain the grasping claws 9 and free end of lead 11 securely in enlarged chamber 14 (FIG. 3).

At this point, it will be helpful to refer to FIGS. 14A-14F, which diagrammatically illustrate in simplied form the heart and vein structure shown in FIG. 11. At this point in the method of the invention, the lead extracting assembly 2 is positioned generally as indicated in FIG. 14A. Reference numeral 65 designates channel scar tissue in vein 59.

Referring next to FIG. 14B, the physician applies traction or tension to locking head 18 in the direction of arrow 66 to hold it, lead grasping catheter 1, and lead 11 stationary. The outer ensheathing catheter 5 and the dilating catheter 3 within it are moved together into vein 59 in the direction indicated by arrows 67. The leading or proximal end dilating catheter 3 then are slid over the grasped end 11A of lead 11. Rotational torque in the direction of arrows 68 is applied back and forth to knobs 45 and 49, which at this point in the procedure are locked together by pin 53 of FIG. 13. This causes the outward serrations 40A and 43A of dilating catheter 3 and ensheathing catheter 5, respectively, to rotate as indicated by arrows 69. The rotation of the serrations 40A of dilating catheter 3 separate the scar tissue 65 that is adherent to the outer surface of endocardial lead 11. As the rotating dilating catheter 3 is forced further into vein 59 and scar tissue 65, the tapered portion 3A dilates the scar tissue, forming a channel therethrough. Eventually, the outward serrations 43A of ensheathing catheter 5 further dilate the channel through the scar tissue 65. Note that up to this point, the position of endocardial lead 11 in the right ventrical 56 of the patient's heart has been unchanged, and tip 51 remains embedded in scar tissue in the myocardial wall.

Referring to FIG. 14C, the previously described advancing of dilating catheter 3 and ensheathing catheter 5 continues under fluoroscope control until the radiopaque tip 39 is determined to be positioned immediately adjacent to embedded tip 51. At this point, it can be seen that the handles 45 and 49 and the respective catheters attached thereto have been advanced together over the entire length of the lead grasping catheter, so that the free end of endocardial lead 11 extends out of the hole at the upper end of inner knob 45. All of the scar tissue along the venous path 59 has been separated from the lead and dilated, and the entire endocardial lead 11 except tip 51 now is located inside dilating catheter 3. Tip 51 remains embedded by scar tissue in the trabeculations of the myocardial wall.

Referring now to FIG. 14D, the next step is to remove pin 53 (see FIG. 13). Then, outer knob 49 is slid forward relative to inner knob 45 in the direction indicated by arrow 79 from the position indicated by dotted line 77 to the position indicated by reference numeral 49. As this is done, outer knob 49 is rotated in the direction of arrows 75. The scale 46 (see FIG. 13) printed along inner handle 45 is carefully observed. Also, the radiopaque portion 42 of the tip 42 of ensheathing catheter 5 can be carefully visualized under fluoroscopic control. The rotation of knob 49 with inner handle 45 being held stationary results in rotation of the sharp outward serrations 43A, causing them to help rotate and thereby separate a cylindrical region in the scar tissue from embedded tip 51 if this scar tissue is not simply torn loose and pushed away from tip 51 in response to the downward force applied to that scar tissue by the smooth, blunt leading edge 43 of catheter 5, (which also guards against accidental cutting of a hole in the myocardial wall). Observation of the scale 46 and utilization of a stop 81 which is on the lower end of inner knob 45 limits the downward movement of outer knob 49 and prevents outward serrations 43A and smooth edge 43 of ensheathing catheter 5 from damaging the wall of the heart.

FIG. 14E shows a cutaway enlarged view of the outward serrations 43A separating the scar tissue that lodges tip 51 in the myocardial wall. In FIG. 14E it can be seen that the leading edge 43 of enseating catheter 5 forces tines 51A forward. In some instances, this forward flexing of tines 51A contributes greatly to dislodging the tip and electrode thereof from the scar tissue.

Ordinarily, even for porous lead tips which are sometimes used, the scar tissue connecting the extreme end of the tip 51 to the myocardial wall is weak enough that the entire lead extraction assembly 2, with the endocardial lead 11 and tip 51 therein can be simply withdrawn out of right ventrical 56 and through the venous pathway 59 in the direction of arrows 70, as shown in FIG. 14F. After the entire assembly and lead have been withdrawn from vein 59, the lead removal process has been completed—without opening the chest of the patient and incurring the risks attendant such operative procedures.

If the lead 11 is broken either in the venous pathway 59 or in a chamber such as 56 of the patient's heart, the above-described procedure is modified by introducing the lead extraction assembly 2 into the vein in a manner which is somewhat conventional in that leads are sometimes introduced in this manner. The first step is to stick an 18 gauge (for example) hollow needle through an appropriate point of vein 59. Next, a flexible guide wire of the type supplied with an introducer known as a "COOK introducer" is inserted through the hollow 18 gauge needle into the venous pathway and is guided, with the aid of X-ray visualization, to the free end of the broken lead 11 to be extracted. The 18 gauge needle then is removed by pulling it outward from the vein and sliding it over the guide wire of the COOK introducer, which is held in its place so that its proximal tip remains adjacent to the free end of the broken lead 11 in the patient's vein or heart cavity. Next, the dilating catheter is slipped over the guide wire, along with an ensheathing catheter of the COOK introducer disposed over the dilating catheter thereof. The COOK introducer then is slid over the guide wire into the vein, so that the leading portion of the COOK introducer follows the guide wire to a location adjacent to the free end of broken lead 11. The guide wire and the dilating catheter are slid out of the ensheathing catheter of the Cook introducer, thereby leaving an open channel through the venous pathway to the free end of the broken lead.

The lead extracting assembly 2 of the present invention then is inserted through the open pathway of the ensheathing catheter until the leading end 7, which is radiopaque in this embodiment of the invention, is positioned adjacent to the free end of the broken lead 11. The grasping mechanism (e.g., the claw arrangement of FIG. 1 or the loop arrangement of FIGS. 6A, B or the basket arrangement of FIGS. 15A, B, C) is extended by means of the distal end of the stylet wires 9A around the free end of the broken lead and manipulated to engage the free end, draw it into the chamber 14 of the dilating catheter 1, and bend the stylet wires 9A around the stylet locking head 18 into the grooves 19 thereof, as previously explained.

Once the free end of the broken lead 11 has been thus grasped, drawn into chamber 14, and made essentially integral with the lead grasping catheter 1, the remaining steps in the process of extracting that lead are the same as previously described for advancing the dilating catheter 3 and the ensheathing catheter 5 to further dilate the venous pathway, if necessary, and cut through scar tissue surrounding the embedded tip 59 and then remove the lead extracting assembly 2 and lead 11 therein as a unit through the ensheathing catheter of the COOK introducer.

It should be noted that in some cases, outward serrations on the lips of the dilating and/or ensheathing catheters might not be needed at all, on either the dilating catheter 3 or the ensheathing catheter 5. Furthermore, in some instances, the dilating catheter might be omitted, and the ensheathing and the lead grasping catheter might be the only ones required. This could be the situation if it is known that there is not a significant amount of scar tissue in the venous pathway. In this event, only the outer ensheathing catheter with its serrated leading edge 43 need be disposed about the lead grasping catheter 1 in order to cut the scar tissue embedding the tip 51 in the myocardial wall tissue. Alternatively, if it is known that the tip 51 is not tightly lodged by scar tissue to the myocardial wall, or if one of the above-mentioned Medtronic screw-in/screw-out tips is utilized, the outer ensheating catheter can be omitted, but the dilating catheter might be needed to separate channel scar tissue in the venous pathway from the outer surface of the lead before it can be rotated tounscrew in electrodes.

It is plausible that a lead grasping apparatus which is not a catheter at all can be used if the free end of the endocardial lead to be removed is available at the connection point to the pulse generator. The grasping tip could be manually clamped to the available free end of the endocardial lead at the proximal end of the lead grasping apparatus, rather than by means of control stylets passing through the center of a lead grasping catheter. In this case, the catheter sheath portion of the lead grasping apparatus is not needed. However, it must be long enough to extend entirely through the distal end of the dilating catheter so that the distal end of the lead grasping apparatus can be held stationary to maintain both the lead grasping mechanism and the endocardial lead grasped thereby substantially stationary as the dilating catheter and the ensheathing catheter are advanced through the venous path into the heart.

In the event that a composite dual lead assembly of the type described in my U.S. Pat. No. 4,332,259 is in place in the patient and needs to be removed, the above-described lead extracting assembly 2 can be utilized, but first it is necessary to sever one of the leads of the composite assembly from the other. In order to understand how this is done, a brief description of the composite lead assembly is necessary. Referring now to FIG. 16A, dual composite lead assembly 100 includes a channel lead 101 and a core lead 102. Typically, the lower portion of the channel lead 101 extends into the coronary sinus or the atrial appendage of the patient's heart, an the core lead 102 extends to a tip that is embedded in the trabeculations of the myocardial wall in the right ventricle. The core lead exits through a side port 103 in the channel lead, as described in more detail in U.S. Pat. No. 4,332,259 issued June 1, 1982 to the present inventor, and incorporated herein by reference.

In accordance with the present invention, since the dilating catheter 3 cannot slide beyond the junction at which the core lead 102 departs from the channel lead 101, it is necessary prior to the utilization of the lead extracting assembly 2, to introduce a COOK introducer (not shown) into the vein (in the manner previously explained) to provide an open-channel sheath or shaft from the venous access point to a point at which it is desired to sever the core lead 102. Once the open channel sheath of the COOK introducer is in place, another catheter 105 is inserted through the open sheath so that its lower end 105A is adjacent to the portion of core lead 102 to be severed, as illustrated in FIG. 16A. At this point, it will be helpful to refer to FIG. 16B, which is a sectional view of the lower portion 105A of catheter 105. Lower catheter section 105A has a sickel-shaped retractable knife 106 therein with a very sharp inner knife edge 106A. The upper portion of sickel-shaped knife 106 is attached to a stylet 108 that extends through the center of catheter 105 and can be manipulated from the distal end of catheter 105 to extend or retract knife 106.

A pair of spaced bars 109 are rigidly disposed inside the lower opening of catheter 105A and act as a pair of stops between which knife 106 extends.

In use, the metal knife 106, which can be visualized by fluoroscopy, is positioned so that its knife edge 106A loops around a portion of core lead 102, as shown in FIG. 16A. The surgeon then applies tension on stylet 108 at the distal end of catheter 105 to produce a force 110 thereon. The force 110 is counterbalanced by an opposite force 111 applied to the catheter 105. This causes core lead 102 to be drawn up against stops 109. As the surgeon increases the tension on stylet 108, the razor-sharp knife edge cuts through core lead 102 as knife edge 106 moves upward in the direction indicated by arrow 112. At this point, catheter 105 and knife 106 therein can be withdrawn. The lower portion of lead 102 is thus free, and can be subsequently grasped by means of a lead grasping mechanism of lead grasping catheter 102 in the manner previously described. If desired, core lead 102 can be withdrawn into the channel of channel lead 101 in the direction indicated by arrow 113. Then the techniques previously described can be utilized to extract both channel lead 100 and the lower portion of core lead 102 from the patient.

Although the above-described lead extracting assembly and techniques for its use do not eliminate all of the risks previously attendant to lead extraction, the procedures and apparatus described herein are believed to substantial reduce the risks which are attendant to previous methods of lead extractions, especially open chest surgery.

While the invention has been described with reference to several particular embodiments thereof, those skilled in the art will be able to make various modifications to the described apparatus and methods without departing from the true spirit and scope of the invention.

I claim:

1. An apparatus for removing an endocardial lead from the heart of a patient via a venous path, said endocardial lead having a free end and a distal end with a tip that is lodged in tissue in said heart, said apparatus comprising in combination:
   (a) first catheter means, having a distal end and a proximal end, for insertion into a venous path to said heart;
   (b) lead grasping means for grasping a portion of said endocardial lead distant from said tip;
   (c) stylet means extending entirely through the length of said first catheter means and connected to said lead grasping means for manipulating of said lead grasping means from said proximal end of said first catheter means and drawing of said lead grasping means and a grasped portion of said endocardial lead into said distal end of said first catheter means and lodging said grasped portion of said endocardial lead in said distal end of said first catheter means;
   (d) stylet tension maintaining means disposed at the proximal end portion of said first catheter means for maintaining sufficient tension on said stylet means to cause said lead grasping means and said grasped portion of said endocardial lead to remain lodged inside of said distal end of said first catheter means and insecurely attached relationship to said distal end of said first catheter means;
   (e) second catheter means disposed concentrically about said first catheter means for controlled advancement over said first catheter means and said endocardial lead toward said tip and for engaging the tissue surrounding said tip and pushing said tissue surrounding said tip away from said tip to separate that tissue from said tip, said second catheter means having a distal end and a proximal end;
   (f) first means for effecting controlled advancing of said second catheter means over said first catheter means and said endocardial lead toward said tip; and
   (g) second means for effecting controlled advancing of said distal end of said second catheter means over said distal end of said first catheter means into sid tissue surrounding said tip and for effecting controlled rotation of said second catheter means relative to said first catheter means, to further effectuate said separating of said tissue from said tip.

2. A method of removing an endocardial lead from the heart of a patient via a venous path, said endocardial lead having a free end and a distal end with a tip that is lodged in tissue in said heart, said method comprising the steps of:
   (a) providing a lead grasping assembly including a first catheter having a proximal end and a distal end, lead grasping means for grasping a portion of said endocardial lead, and stylet means extending entirely through the length of said first catheter for controlling said lead grasping means, the portion of said stylet means extending from said distal end of said first catheter being connected to said lead grasping means;
   (b) providing a second catheter concentrically about said first catheter, said second catheter having a proximal end and a distal end;
   (c) passing said lead grasping assembly through a venous path to advance said lead grasping means to said free end of said endocardial lead;
   (d) manipulating said stylet means at said proximal end of said first catheter to cause said lead grasping means to grasp said free end of said endocardial lead;
   (e) manipulating said proximal end of said second catheter to advance said distal end of said second catheter over said distal end of said first catheter, said lead grasping means, and said free end of said endocardial lead and toward said tip to cause said distal end of said second catheter to engage tissue surrounding said lodged tip and push said tissue away from said tip to separate said tissue from said tip; and
   (f) withdrawing said lead grasping assembly to remove said endocardial lead from said heart.

3. An apparatus for removing an elongated foreign article from a patient's body via a venous path, said apparatus comprising in combination:
   (a) a first catheter, having a distal end and a proximal end, for insertion into a venous path in the patient's body;
   (b) grasping means for grasping a portion of said elongated foreign article;
   (c) stylet means having a proximal end and a distal end and extending entirely through the length of said first catheter and connected to said grasping means for manipulating of said grasping means from said proximal end of said first catheter and drawing of said grasping means and a grasped portion of said elongated foreign article into an enlarged opening in said distal end of said first catheter means, said grasped portion of said elongated foreign article being small enough and/or flexible enough to allow said grasped portion to be drawn into said enlarged opening in said distal end of said first catheter means; and
   (d) stylet tension maintaining means disposed at the proximal end portion of said first catheter for maintain sufficient tension on said stylet means to retain said grasping means and said grasped portion of said elongated foreign article in said enlarged opening in said distal end of said first catheter and in securely attached relationship to said distal end of said first catheter, such that said first catheter effectively becomes an extension of said elongated foreign article.

4. The apparatus of claim 3 wherein said stylet means includes a semi-rigid second catheter extending through said first catheter, and said stylet means also includes a flexible stylet wire extending through said second catheter, and said grasping means includes a plurality of flexible, elongated spring members distinct from said stylet means and each having a first end and a second end, the first end of each of said spring members being attached to said distal end of said second catheter, the second end of each of said spring members being connected to said distal end of said stylet wire, said manipulation of said stylet means from said proximal end of said first catheter means causing flexing of said spring members to cause the midportions of said spring members to bow outwardly to form a basket and then return to a collapsed configuration wherein a portion of said elongated foreign article is ensnared between two adjacent ones of said spring members.

5. The apparatus of claim 4 wherein said spring members are initially substantially straight, and are bowed outwardly by pulling on said proximal end of said stylet means, and are collapsed to ensnare said elongated foreign article by releasing or pushing said proximal end of said stylet means.

6. A method for removing an elongated foreign article from a patient's body via a venous path, said method comprising the step of:
(a) providing a first catheter for insertion into a venous path in the patient's body, said first catheter having a proximal end and a distal end;
(b) providing a grasping means for grasping a portion of said elongated foreign body;
(c) providing a stylet means extending entirely through the length of said first catheter, a distal end of said stylet being connected to said grasping means to effectuate manipulating of said grasping means from said proximal end of said first catheter and drawing of said grasping means and a grasped portion of said elongated foreign article into an enlarged opening in said distal end of said first catheter, said grasped portion of elongated foreign article being small enough and/or flexible enough to allow said grasped portion to be drawn into said enlarged opening in said distal end of said first cather;
(e) passing said first catheter, said grasping means and said stylet means into the venous path to advance a portion of said grasping means to a portion of said elongated foreign article;
(f) manipulating a proximal end of said stylet to open a grasping portion of said grasping means and close it upon a portion of said elongated foreign article;
(g) pulling said grasping means and the grasped portion of the elongated foreign article into said enlarged opening and maintaining tension on said stylet means to draw said lead grasping means and said grasped portion of said elongated foreign object into said enlarged opening and maintain said elongated foreign object in securely attached relationship with the distal end of said first catheter so that first catheter effectively becomes an extension of said elongated foreign object; and
(h) withdrawing said first catheter, said grasping means said stylet, and said elongated foreign object as a unit out of said venous path.

7. The method of claim 6 including providing a semi-rigid second catheter extending through said first catheter and a flexible stylet wire extending through said second catheter, and providing on said grasping means a plurality of flexible, elongated spring members distinct from said stylet means and each having a first end attached to a peripheral end portion of said second catheter and a second end attached to a distal end of said stylet wire, said method including pulling on said stylet means from said proximal end of said first catheter to cause flexing of said spring members to cause their midportions to bow outwardly to form a basket, and causing said means to move said distal end of the stylet wire outward to cause said spring members to return to a collapsed configuration wherein the grasped portion of the elongated foreign article is ensnared between two adjacent spring members.

* * * * *